US012789012B2

(12) United States Patent
Asmerom et al.

(10) Patent No.: US 12,789,012 B2
(45) Date of Patent: Nov. 10, 2026

(54) HEAD IMMOBILIZER APPARATUS AND METHODS OF IMMOBILIZING A PATIENT'S HEAD DURING RADIOTHERAPY

(71) Applicant: Zap Surgical Systems, Inc., San Carlos, CA (US)

(72) Inventors: George Asmerom, San Jose, CA (US); Michael W. McDermott, Miami, FL (US); Aizik L. Wolf, Miami, FL (US); John R. Adler, Jr., Stanford, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 271 days.

(21) Appl. No.: 18/654,897

(22) Filed: May 3, 2024

(65) Prior Publication Data

US 2024/0374931 A1 Nov. 14, 2024

Related U.S. Application Data

(60) Provisional application No. 63/465,998, filed on May 12, 2023.

(51) Int. Cl.
*A61N 5/10* (2006.01)

(52) U.S. Cl.
CPC .... *A61N 5/1077* (2013.01); *A61N 2005/1097* (2013.01)

(58) Field of Classification Search
CPC .......... A61N 5/1077; A61N 2005/1097; A61N 5/1049
USPC ............................................ 250/492.1–492.3
See application file for complete search history.

(56) References Cited

U.S. PATENT DOCUMENTS

| | | | |
|---|---|---|---|
| 4,463,758 | A | 8/1984 | Patil et al. |
| 5,879,281 | A | 3/1999 | Ein-gal |
| 8,337,382 | B2 | 12/2012 | Schneider et al. |
| 8,747,292 | B2 | 6/2014 | Schneider et al. |
| 9,808,651 | B2 | 11/2017 | Schneider et al. |
| D843,582 | S | 3/2019 | Adler et al. |
| 10,499,861 | B2 | 12/2019 | Achkire et al. |
| D900,838 | S | 11/2020 | Bodduluri et al. |

(Continued)

OTHER PUBLICATIONS

Leksell , et al., "A new fixation device for the Leksell stereotaxic system", J Neurosurg 66, 1987, pp. 626-629.

*Primary Examiner* — Michael Maskell
(74) *Attorney, Agent, or Firm* — Kilpatrick Townsend & Stockton LLP

(57) ABSTRACT

Various embodiments of a head immobilization apparatus and systems and methods of using the head immobilization apparatus are described herein. The apparatus includes a base configured for underlying a patient's head during radiotherapy and a fixation device including a left arm portion that extends alongside a left side of the patient's head and a right arm portion that extends alongside a right side of the patient's head. The fixation device includes a rotational joint through which the left arm portion is coupled to the base and a rotational joint through which the right arm portion is coupled to the base. The rotational joints are configured to facilitate pivoting adjustment of the fixation device within a coordinate system defined by the radiotherapy treatment system to accommodate a position of the patient's head to facilitate immobilization of the patient's head during radiotherapy.

35 Claims, 13 Drawing Sheets

(56) References Cited

U.S. PATENT DOCUMENTS

| | | | | |
|---|---|---|---|---|
| 11,058,892 | B2 | 7/2021 | Wilbur et al. | |
| D928,820 | S | 8/2021 | Bodduluri et al. | |
| 2016/0317103 | A1 * | 11/2016 | Yakacki ................. | A61B 5/055 |
| 2020/0345572 | A1 * | 11/2020 | Cooke .................... | A61B 5/702 |

* cited by examiner

HEAD IMMOBILIZER APPARATUS AND METHODS OF IMMOBILIZING A PATIENT'S HEAD DURING RADIOTHERAPY

CROSS-REFERENCES TO RELATED APPLICATIONS

The present application claims the benefit of priority of U.S. Provisional Application Ser. No. 63/465,998, filed May 12, 2023; the full disclosure which is incorporated herein by reference in its entirety.

BACKGROUND OF THE INVENTION

Various treatments, including radiotherapy treatments and imaging associated with these treatments, require immobilization of a patient or a portion of the patient's body. There is a need in the art for improved devices which are capable of immobilizing patients or patient anatomies. In particular, various radiotherapy medical procedures involve repeated accurate positioning (e.g., fixation) of a patient or a portion of patient's body. Thermoplastic sheets (e.g., also known as masks) are used as patient immobilizers in radiation therapy to reduce or prevent movement of the patient or a portion of the patient's body during therapy. These sheets are heated to become formable and are formed to the patient for immobilizing the patient once the sheet is cooled to harden. These "mask" technologies have limited capability for restraining movement in patients with involuntary (e.g., uncontrollable) movement disorders such as a dystonia, an essential tremor, Huntington's disease, multiple system atrophy (MSA), myoclonus, Parkinson's disease, Progressive Supranuclear Palsy (PSP), Tourette syndrome, etc.

Further established approaches for immobilizing a patient's head during radiotherapy include more devices that include cumbersome support frames having a skeleton of surgical steel. For example, movement may be prevented entirely by fixing the patient (for example, their head) in place with fixation means such as a stereotactic frame that defines a coordinate system. This approach of rigid fixation is also used with the Gamma Knife (Elekta, Stockholm, Sweden). Stereotactic frames have substantial space requirements which are difficult for physicians to maneuver around and difficult to position within the radiotherapy system and require the coordinate system of the frame dictate the coordinate system of the subsequent stereotactic radiosurgery.

BRIEF SUMMARY OF THE INVENTION

In one embodiment, the invention pertains to head immobilization devices (e.g., a head immobilizer, a fixation device), systems, and methods for immobilizing a patient's head in a radiotherapy treatment system during therapy and/or in an image-based anatomy matching system during imaging. In some embodiments, the fixation device is adjustable to the patient's head positioned according to predefined coordinates of the system(s). This allows the fixation device to accommodate a position of the patient's head to facilitate immobilization of the patient's head during treatment. In some embodiments, this immobilization device, or a replica thereof, can further be used during imaging so that a patient's position during imaging corresponds to the immobilized position during radiotherapy.

In one embodiment, a head immobilization apparatus for immobilizing a patient's head in a radiotherapy treatment system during radiotherapy includes a base for underlying a patient's head during radiotherapy and a fixation device for immobilizing the patient's head during radiotherapy. The fixation device is coupled to and extends upwards from the base, The fixation device includes a left arm portion that extends alongside a left side of the patient's head and a right arm portion that extends alongside a right side of the patient's head when the fixation device is positioned on the patient's head for immobilization during radiotherapy. The fixation device includes one or more apertures disposed within each of the left arm portion and the right arm portion of the fixation device that are each aligned with the patient's head so that one or more pins extending through the one or more apertures engage the patient's head to facilitate immobilization during radiotherapy. The fixation device includes a first rotational joint through which the left arm portion is coupled to the base and a second rotational joint through which the right arm portion is coupled to the base. The rotational joints facilitate pivoting adjustment of the fixation device within a coordinate system defined by the radiotherapy treatment system to accommodate a position of the patient's head to facilitate immobilization of the patient's head during radiotherapy.

In some embodiments, the left arm portion is coupled to the base through a sliding joint and the right arm portion is further coupled to the base through a sliding joint. The sliding joints are used to slide the fixation device in a direction parallel to a longitudinal axis of the patient such that the fixation device can slide in a longitudinal direction to adjust a position of the fixation device relative to the patient's head. In other embodiments, the sliding joints slide the fixation device is a direction substantially parallel to a longitudinal axis of the patient such that the fixation device can slide in longitudinal direction to adjust a position of the fixation device relative to the patient's head. For example, the fixation device is slightly angled toward the base (e.g., less than or equal to a 5 degree offset). In some embodiments, a pivot mount connects each arm portion to the base and each pivot mount includes the rotational joint and the sliding joint. In one embodiment, the pivoting adjustment includes adjustment of an incline of the fixation device relative to the base. One or both rotational joints of the left and right arm portions may include markings indicative of the incline of the fixation device relative to the base. Each of the left arm portion and the right arm portion of the fixation device may include at least four apertures. In some embodiments, each of the left arm portion and the right arm portion of the fixation device includes at least two sets of apertures. A more proximate set may be disposed behind an car on the patient's head and a more distal set may be disposed at a temple on the patient's head. Each of the at least two sets of apertures may include at least two apertures. Each of the at least two sets of apertures may include at least four apertures. Each of the apertures may receive a pin therein for securing a position of the head of the patient when the patient is immobilized by the apparatus. The pins may extend through the apertures and engage the head of the patient at an angle of greater than or equal to 90 degrees when the patient is immobilized by the apparatus. Each pin has a major component in a horizontal direction.

In some embodiments, the fixation device further includes a connecting portion connecting the left arm portion and the right arm portion of the fixation device. The connecting portion is removably coupled to the left and/or right arm portions. The fixation device may extend across the head of a patient when the patient is positioned on the base. In other embodiments, the left arm portion, the right arm portion, and the connecting portion of the fixation device form a unitary component of the fixation device.

In one embodiment, a head rest is disposed atop the base. The head rest is configured to support the head of the patient when the patient is positioned on the base. The base may include a planar surface. In some embodiments, the base may be a base plate for use with the fixation device. In other embodiments, the base is part of a table or other surface on which the patient is positioned.

In one embodiment, a method for immobilizing a head of a patient during a radiation therapy session includes positioning the patient's head in a radiotherapy treatment system such that the patient's head is disposed on a base of a fixation device. The method further includes adjusting the fixation device relative to the patient's head within a coordinate system defined externally of the fixation device of the treatment system to accommodate a position of the patient's head. The method also include advancing at least one pin to center from each of opposite lateral sides of the fixation device to center and engage the patient's head to affix the patient's head in the position and performing the radiation therapy while the patient's head is immobilized by the fixation device whereby excessive movement of the patient's is prevented during the radiation therapy.

In one embodiment, the method also includes adjusting an incline of the fixation device relative to the base. The base may be substantially horizontal. Adjusting the fixation device may further include sliding the fixation device relative to the base.

In one embodiment, the method further includes, prior to performing the radiation therapy, positioning the patient's head in a desired position, adjusting a fixation device of another immobilization device within a predefined coordinate system of an imaging system, and performing an imaging process of the head of the patient. The other immobilization device used for imaging may be a replica of the immobilization device used for radiotherapy, the replica being substantially the same in size and configuration as the immobilization device. The method may also include disposing a mask between the patient and the fixation device during the imaging process and/or the radiation therapy. The mask may be placed over the patient's head prior to the imaging and/or the radiation therapy.

In one embodiment, a treatment system includes an image-based anatomy matching system using a predefined coordinate system and a head immobilization device. The head immobilization device includes a base and a fixation device, the fixation device being adjustable relative to the base to an external coordinate system to accommodate and immobilize a patient's head positioned within an externally defined coordinate system of the image-based anatomy matching system.

In some embodiments, the left arm portion is coupled to the base through a sliding joint and the right arm portion is further coupled to the base through a sliding joint. The sliding joints are used to slide in a direction parallel to a longitudinal axis of the patient such that the fixation device can slide in a longitudinal direction to adjust a position of the fixation device relative to the patient's head. In some embodiments, a pivot mount connects each arm portion to the base and each pivot mount includes the rotational joint and the sliding joint. In one embodiment, the pivoting adjustment includes adjustment of an incline of the fixation device relative to the base. One or both rotational joints of the left and right arm portions may include markings indicative of the incline of the fixation device relative to the base. Each of the left arm portion and the right arm portion of the fixation device may include at least four apertures. In some embodiments, each of the left arm portion and the right arm portion of the fixation device includes at least two sets of apertures. A more proximate set may be disposed behind an ear on the patient's head and a more distal set may be disposed at a temple on the patient's head. Each of the at least two sets of apertures may include at least two apertures. Each of the at least two sets of apertures may include at least four apertures. Each of the apertures may receive a pin therein for securing a position of the head of the patient when the patient is immobilized by the apparatus. The pins may extend through the apertures and engage the head of the patient at an angle of greater than or equal to 90 degrees when the patient is immobilized by the apparatus. Each pin has a major component in a horizontal direction.

In some embodiments, the fixation device further includes a connecting portion connecting the left arm portion and the right arm portion of the fixation device. The connecting portion is removably coupled to the left and/or right arm portions. The fixation device may extend across the head of a patient when the patient is positioned on the base.

DETAILED DESCRIPTION OF THE INVENTION

Figure 1:
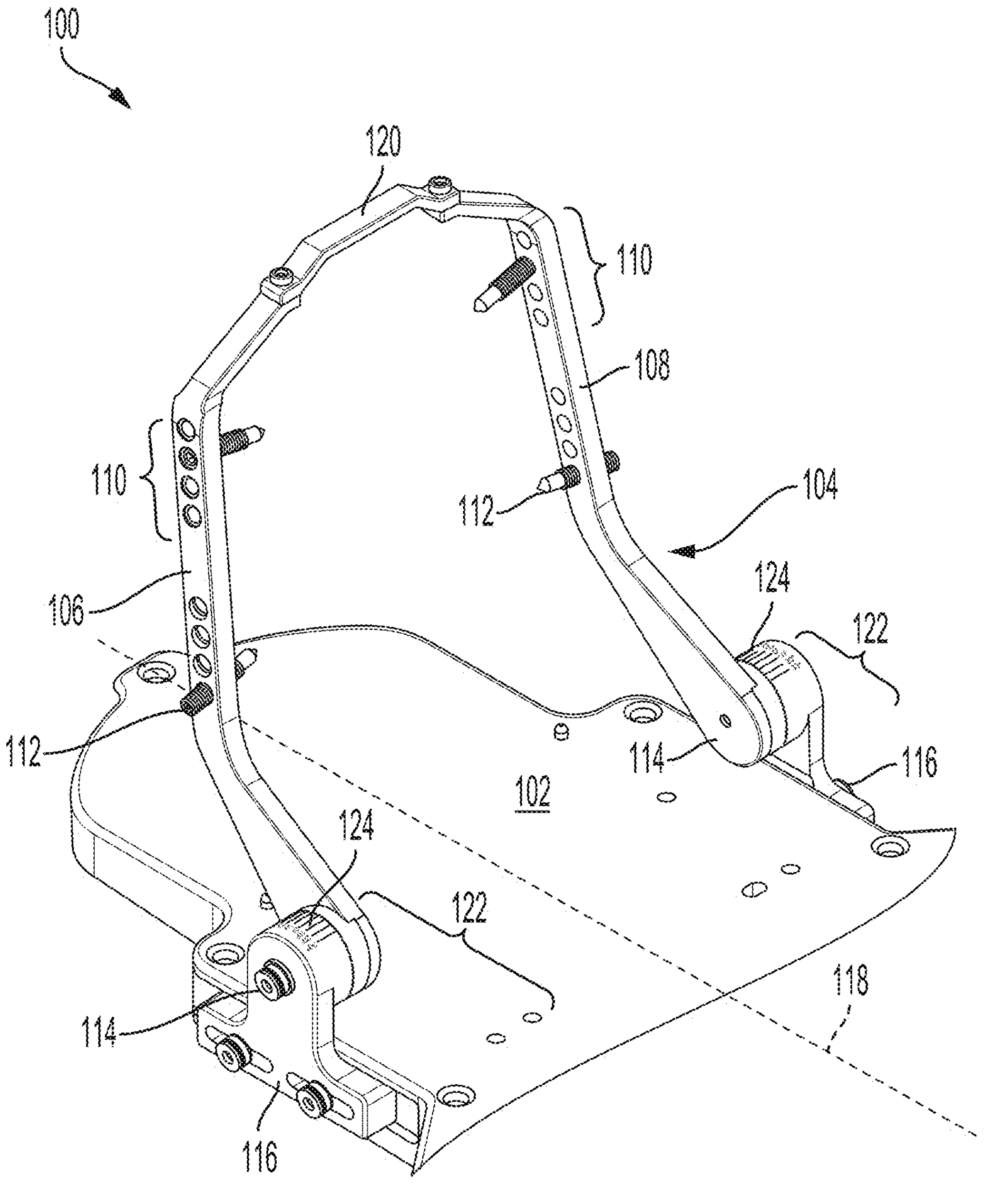
FIG. 1 is perspective drawing of an exemplary head immobilization device, in accordance with one aspect of the present disclosure.

The accompanying drawings, which are incorporated herein and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and can or cannot represent actual or preferred values or dimensions.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) can be practiced without those specific details. In some instances, well-known structures and components can be shown in block diagram form in order to avoid obscuring the concepts of the disclosed subject matter. In the drawings, like reference numerals represent like parts throughout the several views.

Presently available stereotactic frames, such as Leksell's stereotactic frame, are particularly cumbersome and have limited access to the cranial vault. Leksell, Lars, et al. "A New Fixation Device for the Leksell Stereotaxic System." *Journal of Neurosurgery*, vol. 66, no. 4, 1987, pp. 626-629., https://doi.org/10.3171/jns.1987.66.4.0626. At the beginning of the procedure, the frame is attached to the patient's head using local anesthetic to numb the scalp. The Leksell stereotactic frame is fixed to the patient's head with adjustable fixation posts placed around the patient's head and secured with weight-bearing pins secured to the head. The stereotactic frame defines a fixed frame of reference and positions the patient's head within predefined coordinates of that fixed frame of reference of the stereotactic frame, which is then positioned and aligned within the stereotactic radiotherapy system.

The Mayfield Head Clamp defines a frame of reference of the system and fixes the patient's head in the frame of reference of the clamp, which is positioned within the radiotherapy system. (Ohio Medical Corp, Cincinnati Ohio, Integra LifeSciences, Plainsboro, NJ). The Mayfield Head Clamp immobilizes the head using weight-bearing pins on each side of the head.

The Elekta Fixation Instrument for GK (Elekta, Stockholm, Sweden), is used, for example, in the Vantage™ Stereotactic System. This stereotactic instrument is a fixation device which defines stereotactic coordinates, thereby defining the frame of reference of the stereotactic system and fixes the patient's head in the frame of reference. The Elekta High Definition Motion Management System (Elekta, Stockholm, Sweden) includes a fixation device which similarly defines stereotactic coordinates, thereby defining the frame of reference of the stereotactic system.

The present invention generally relates to a head immobilization device that immobilizes a patient's head positioned within a predetermined frame of reference (e.g., a coordinate system) of an imaging and/or treatment system. This is in stark contrast to stereotactic frames which define the frame of reference and position the head of the position within that frame of reference, as described in exemplary products above. For example, a head immobilization apparatus, as described herein, may immobilize a patient's head in a radiotherapy treatment system during radiotherapy where a fixation device of the head immobilization apparatus is adjustable to differing positions and alignments within a coordinate system defined by the radiotherapy treatment system to accommodate a position of the patient's head for immobilization.

Advantageously, the fixation device described herein is relatively less bulky than previous designs and adjusts to the patient within any coordinate system, rather than defining the coordinate system itself. For example, the coordinate system may be any externally defined coordinate system. Additionally, the fixation device described herein applies relatively less pressure to the pins engaged with the patient's head as the pins extend in a direction having a major component in a horizontal direction such that the pins do not bear the weight on the patient's head. This considerably improves patient comfort as compared to conventional stereotactic frames and clamps having pins that bear the weight of the patient's head. Furthermore, the fixation device, as described throughout the present disclosure, is relatively easy to sanitize and reuse compared to the bulky stereotactic frames that are difficult to disassemble for sanitation. A method of using the head immobilization device described throughout the present disclosure includes adjusting the fixation device relative to the patient's head, the patient's head being positioned within a predefined frame of reference defined externally of fixation device of the treatment system. Accordingly, the fixation device can accommodate a position of the patient's head within the predefined coordinate system of the radiotherapy and/or imaging system and prevent excessive movement of the patient's head during the procedure.

FIG. 1 is medical device 100 to facilitate positioning of a patient's head to facilitate immobilization of the patient's head during radiotherapy. The medical device 100 may include more or less components than those shown here and may include any combination of components described herein. Components having the same numbering shown in other figures. are assumed to have the same configuration as the components described in relation to this figure.

The medical device 100 is a head immobilization device in various embodiments. In particular, the medical device is a head immobilization apparatus for immobilizing a patient's head in a radiotherapy treatment system during radiotherapy. The medical device 100 includes a base 102 configured for underlying a patient's head during radiotherapy. In some embodiments, the base 102 may be a base plate for use with the fixation device. In other embodiments, the base 102 is part of a table or other surface on which the patient is positioned. The medical device includes a fixation device 104 configured for immobilizing the patient's head during radiotherapy. The fixation device 104 is coupled to and extends upwards from the base 102. In various embodiments, the fixation device 104 is coupled to the base 102 via a fastening mechanism such as a rotational joint and/or a sliding joint, to be described in further detail below, to allow adjustment of the fixation device relative to a predefined frame of reference of a radiotherapy system and/or an imaging system. In other embodiments, the fixation device 104 extends from the base 102 and is adjustable to other positions and/or orientations than that shown in FIG. 1.

In at least some embodiments, the fixation device 104 includes a right arm portion 106 (e.g., from a perspective of the patient) that extends alongside a right side of the patient's head and a left arm portion 108 that extends alongside a left side of the patient's head when the fixation device 104 is positioned on the patient's head for immobilization during radiotherapy. The right arm portion 106 and the left arm portion 108 can each be formed as a single piece (as shown) or the right arm portion 106 and the left arm portion 108 may include multiple pieces.

In various embodiments, one or more apertures 110 are disposed within each of the right arm portion 106 and the left arm portion 108 of the fixation device 104 that are aligned with the patient's head so that one or more pins 112 extend through the one or more apertures 110 and engage (e.g., affix) the patient's head to facilitate immobilization during radiotherapy. The pins 112 may be varying lengths or the same length, in accordance with various embodiments of the present disclosure.

In further embodiments, the right arm portion 106 is coupled to the base 102 through a rotational joint 114 and the left arm portion 108 is coupled to the base 102 through a substantially similar rotational joint 114. The rotational joints 114 are configured to facilitate pivoting adjustment of the fixation device 104 within a coordinate system defined by the radiotherapy treatment system to accommodate a position of the patient's head to facilitate immobilization of the patient's head during radiotherapy.

In at least some embodiments, the right arm portion 106 is coupled to the base 102 through a sliding joint 116 and the left arm portion 108 is coupled to the base 102 through a substantially similar sliding joint 116. The sliding joints 116 are configured to slide in a direction parallel to a longitudinal axis 118 of the base 102 (e.g., of the patient when the patient is positioned on the base 102) such that the fixation device 104 can slide in a longitudinal direction to adjust a position of the fixation device 104 relative to the patient's head so that the one or more apertures 110 are aligned with corresponding points on the patient's head (e.g., on either side of the temple and bony protuberance behind the patient's ears). Each of the rotational joint 114 and the sliding joint 116 may be tightened (e.g., secured) using a known mechanism such as an Allen wrench, a hex head screwdriver, Phillips screwdriver, or any suitable tool. In some embodiments, the sliding joint 116 may be a pin mount where a pin of the right arm portion 106 may be pin mounted relative to the base 102 at a number of positions. The sliding joint 116 for the left arm portion 108 may similarly be a pin mount, according to at least some embodiments.

In the embodiment shown, the fixation device 104 includes a connecting portion 120 connecting the right arm portion 106 and the left arm portion 108 of the fixation device 104. The connecting portion 120 is removably coupled to the right arm portion 106 and/or the left arm portion 108. For example, the connecting portion 120 may be removably coupled using one or more fastening members, including screws, a screw tight fastener, a latch, etc. In various embodiments, the connecting portion 120 may be provided for safety of a patient during procedures. For example, the connecting portion 120 may include a quick release mechanism that enables relatively quick release of the patient from the fixation device 104 in at least some embodiments. In other embodiments, the left arm portion, the right arm portion, and the connecting portion of the fixation device form a unitary component of the fixation device.

In some embodiments, a pivot mount 122 may connect each arm portion (right arm portion 106 and left arm portion 108) to the base 102. The right arm portion 106 and the left arm portion 108 may be coupled to the base 102 via a pivot mount 122 which includes the rotational joint 114 and the sliding joint 116, as shown in FIG. 1. In other embodiments the right arm portion 106 and the left arm portion 108 are directly coupled to the base 102 through the rotational joint 114 and/or the sliding joint 116.

In some embodiments, one or both rotational joints 114 and/or the sliding joints 116 of the right arm portion 106 and the left arm portion 108 include markings 124 indicative of the incline and/or the position of the fixation device 104 relative to the base 102. In particular, in some embodiments, the fixation device 104 may be pivotably adjustable where the incline of the fixation device 104 relative to the base 102 is adjusted. Markings 124 indicate the incline of the plane along which the fixation device 104 extends relative to the base 102. The markings may include angles or degrees of the fixation device 104 relative to a planar surface of the base 102. In one exemplary aspect, the fixation device 104 is set so that the distal portion of each arm portion extends about 90 degrees relative to a planar surface of the base 102 (as shown in FIG. 1) and may be adjusted by approximately 30 degrees in each direction, for example, approximately 20 degrees to 30 degrees to accommodate the patient's head once the patient is positioned on the base 102. Markings 124 may indicate an incline associated with the adjustments. Similarly, the sliding joints 116 may include markings (not shown) which indicate how far forward or backward the fixation device 104 is adjusted relative to an initial position relative to the base 102. For example, if a patient is positioned on the base 102 relatively far forward or backward, the sliding joint 116 on each side of the base 102 may be adjusted to accommodate the patient's head and markings on the sliding joint may facilitate the alignment of the right arm portion 106 and the left arm portion 108 of the fixation device 104.

Various components of the medical device 100 include aluminum and/or titanium. For example, the fixation device 104 includes aluminum and the pins 112 includes titanium. In at least some embodiments, components of the medical device 100 may include carbon fiber and/or engineering plastics as would be appreciated by one having ordinary skill in the art upon reading the present disclosure. In some embodiments, the fixation device 104 is a disposable or reusable. In some embodiments, replicas of the medical device 100 and/or the pins 112 may be used for imaging procedures. Replicas, as referred to throughout the present disclosure, refer to components which are substantially the same in size and configuration as components used during radiotherapy procedures. Replicas may include plastic or other relative soft materials. In some embodiments, a plastic or radio-translucent material is advantageous as it allows use of the immobilization device, at least for alignment purposes, during imaging without interference from non-radiotranslucent materials, such as metal. Replica components may be disposed after use, in at least some embodiments.

Figure 2:
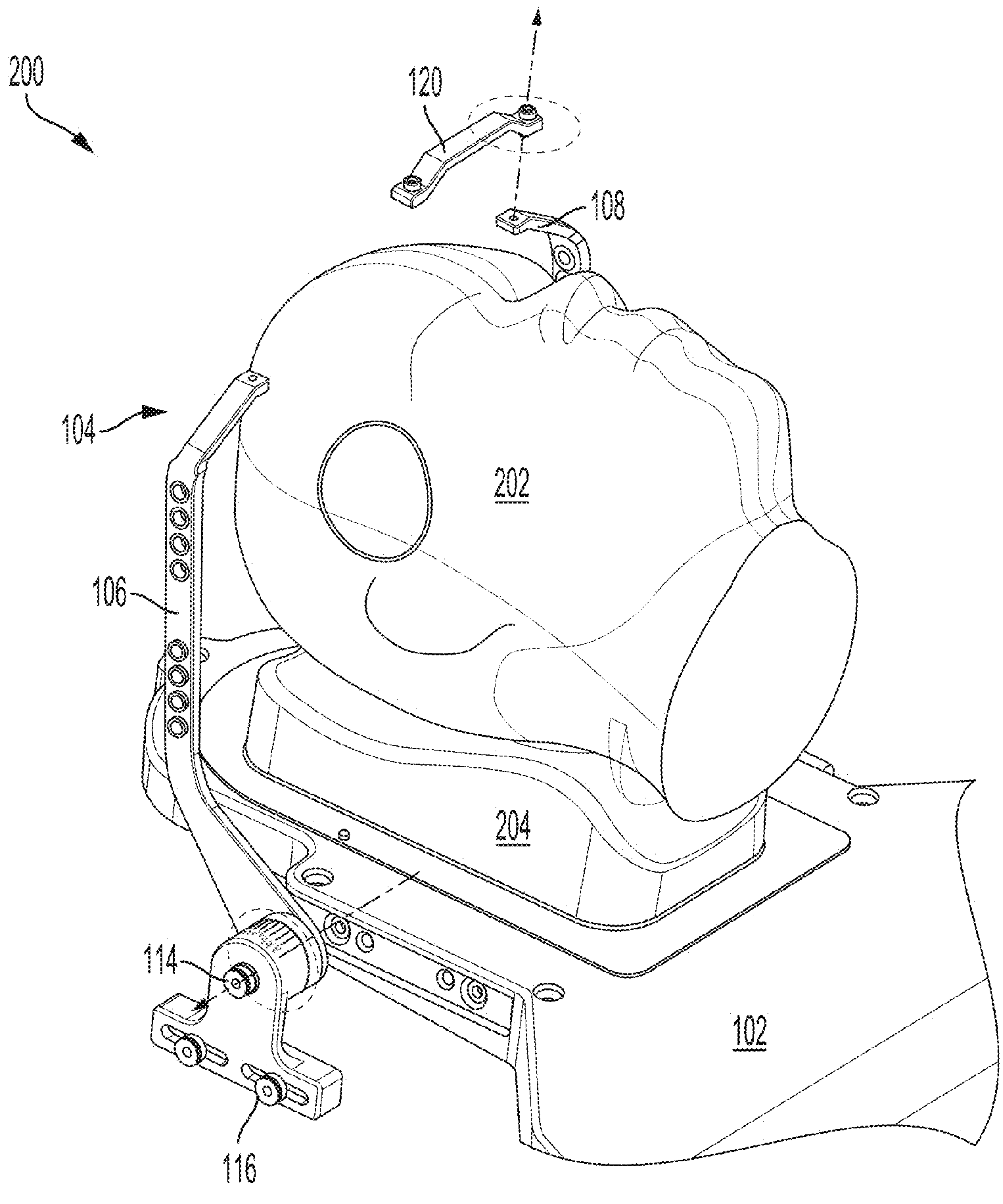
FIG. 2 is perspective drawing of an exemplary head immobilization device, in accordance with one aspect of the present disclosure.

Referring now to FIG. 2, a patient head 202 is shown positioned in an exploded view of a head immobilization device system 200. In various embodiments, the head immobilization device system 200 is used in combination with an image-based anatomy matching system using a predefined coordinate system. Fixation device 104 is adjustable relative to the base 102 to accommodate the patient's head 202, which is positioned within the predefined coordinate system, to immobilize the patient's head 202 within the externally defined coordinate system of the image-based anatomy matching system. As shown, the patient head 202 is positioned on a base 102 as described above. The fixation device 104, in particular the connecting portion 120 and the top portions of the right arm portion 106 and the left arm portion 108, extend around and across the patient head 202 when the patient is positioned on the base 102.

The head immobilization device system 200 may further include a head rest 204 disposed on the base 102. The head rest 204 may be configured to support the patient head 202 when the patient is positioned in the treatment system. In at least some embodiments, the head rest 204 is custom molded or otherwise custom fit to the patient's head to further facilitate immobilizing the patient's head when the patient's head is immobilized by the fixation device 104. For example, a custom molded or otherwise custom fit head rest 204 may engage a greater portion of the patient's head when compared to a patient's head positioned directly on the base 102. In some embodiments, the head rest 204 is a table cushion. The head rest 204 can decrease the weight and/or pressure experienced by the patient. For example, the pins (not shown for simplicity) are not bearing the weight of the patient's head.

Figure 3B:
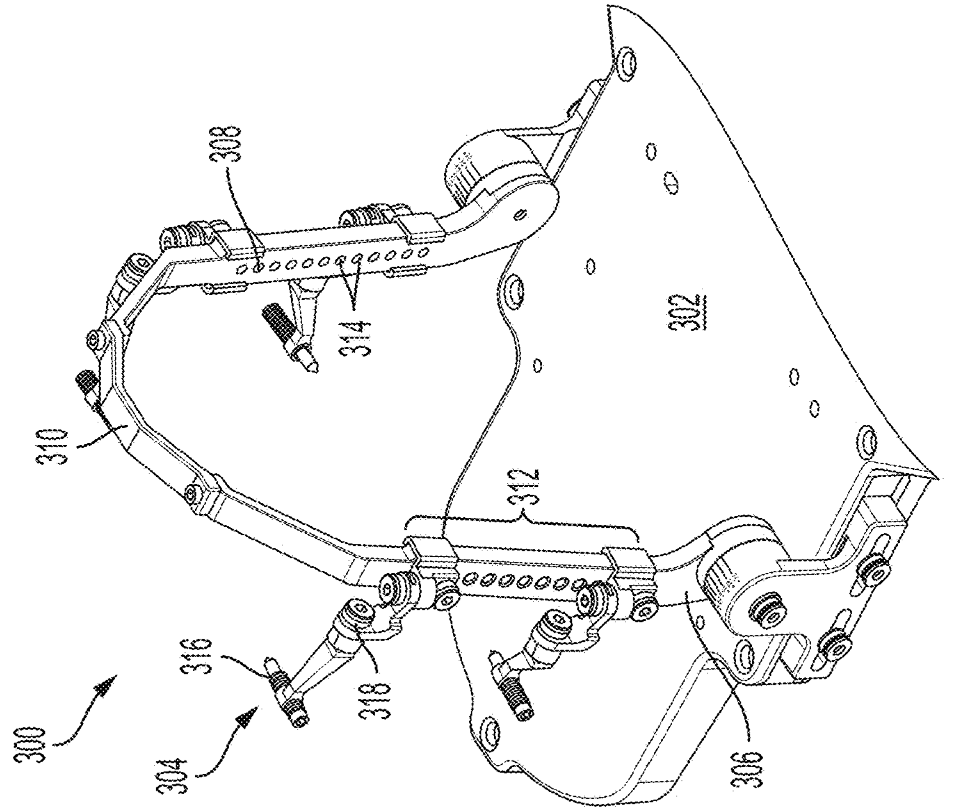
FIG. 3A-3B illustrate alternative exemplary head immobilization devices, in accordance with aspects of the present disclosure.
Figure 3A:
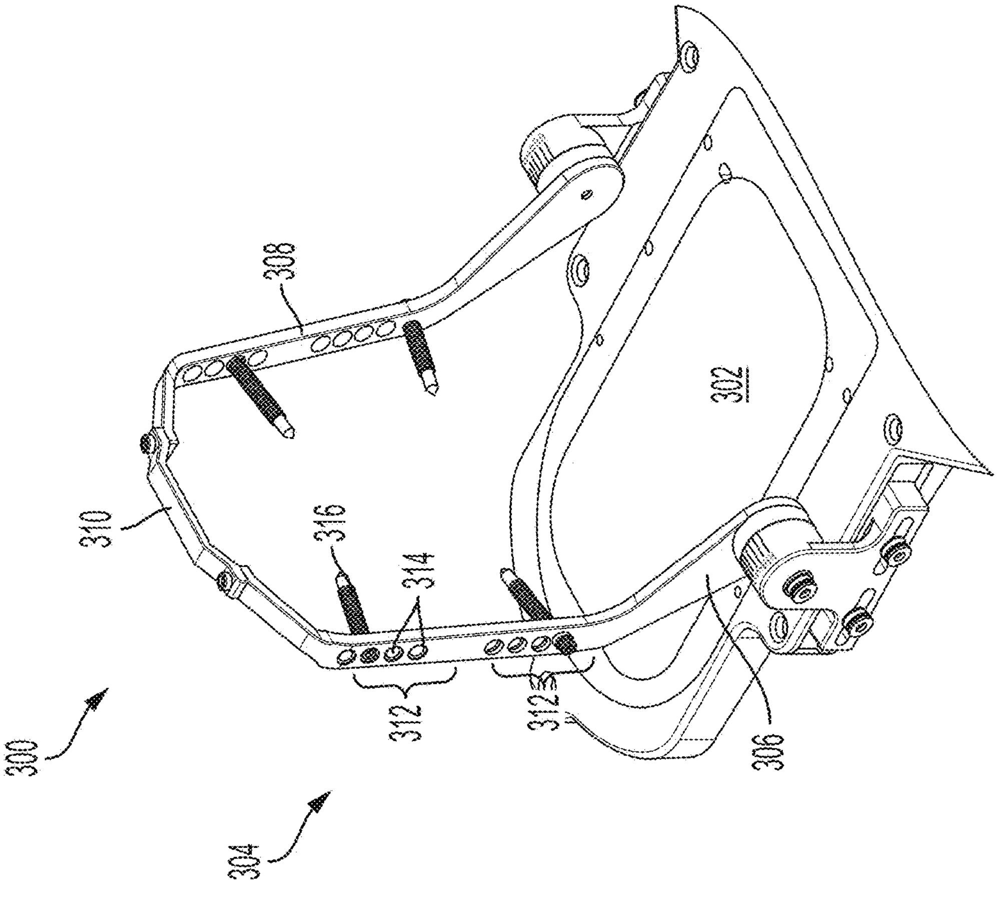

Referring now to FIGS. 3A-3B, various exemplary configurations of a head immobilization device 300 are shown. In general, the head immobilization device 300 includes a base 302, and a fixation device 304 including a right arm portion 306, a left arm portion 308, and a connecting portion 310 similar to those described in detail above.

As illustrated in FIG. 3A, in some embodiments, the head immobilization device 300 (e.g., the fixation device 304 of the head immobilization device 300) includes at least two sets 312 of apertures 314 along each of the right arm portion 306 and the left arm portion 308. As shown, each set 312 of apertures 314 includes at least four apertures 314. In other embodiments, each set 312 of apertures 314 includes at least two apertures 314. Any number or configuration of sets 312 of apertures 314 or apertures 314 may be included in the fixation device 304 (e.g., the right arm portion 306 and the left arm portion 308 of the fixation device 304). The number and/or configuration of apertures 314 or sets 312 of apertures 314 may be optimized for engaging a patient head using pins 316 disposed through at least one aperture 314, at least two apertures 314, etc., on each of the right arm portion 306 and the left arm portion 308. For example, sets 312 of apertures 314 allow the fixation device 104 to accommodate to any patient (e.g., patient head shapes vary significantly). Furthermore, multiple apertures 314 enable the clinician to select an appropriate aperture 314 that is aligned with the target region on the patient's head. In particular, one or more pins 316 extend through the one or more apertures 314 to engage the patient's head to facilitate immobilization of the patient's head during treatment. In the embodiment, shown each set of apertures includes four apertures. In some embodiments, each set includes three apertures. In other embodiments each set includes four or more apertures.

In some embodiments, the head immobilization device 300 (e.g., the fixation device 304 of the head immobilization device 300) includes one set 312 of apertures 314 along each of the right arm portion 306 and the left arm portion 308, as shown in FIG. 3B. As shown, each of the right arm portion 306 and the left arm portion 308 include multiple apertures 314 in one set 312 of apertures 314. In various embodiments, additional arm mounts 318 may extend from each of the right arm portion 306 and the left arm portion 308. In these embodiments, the arm mounts 318 extend through the respective aperture 314 and support a pin 316 for engaging the patient's head. The arm mounts 318 may have one or more rotational joints for adjusting an angle and/or height of the pin 316 with respect to a patient's head when the patient is positioned on the base 302.

Figure 4:
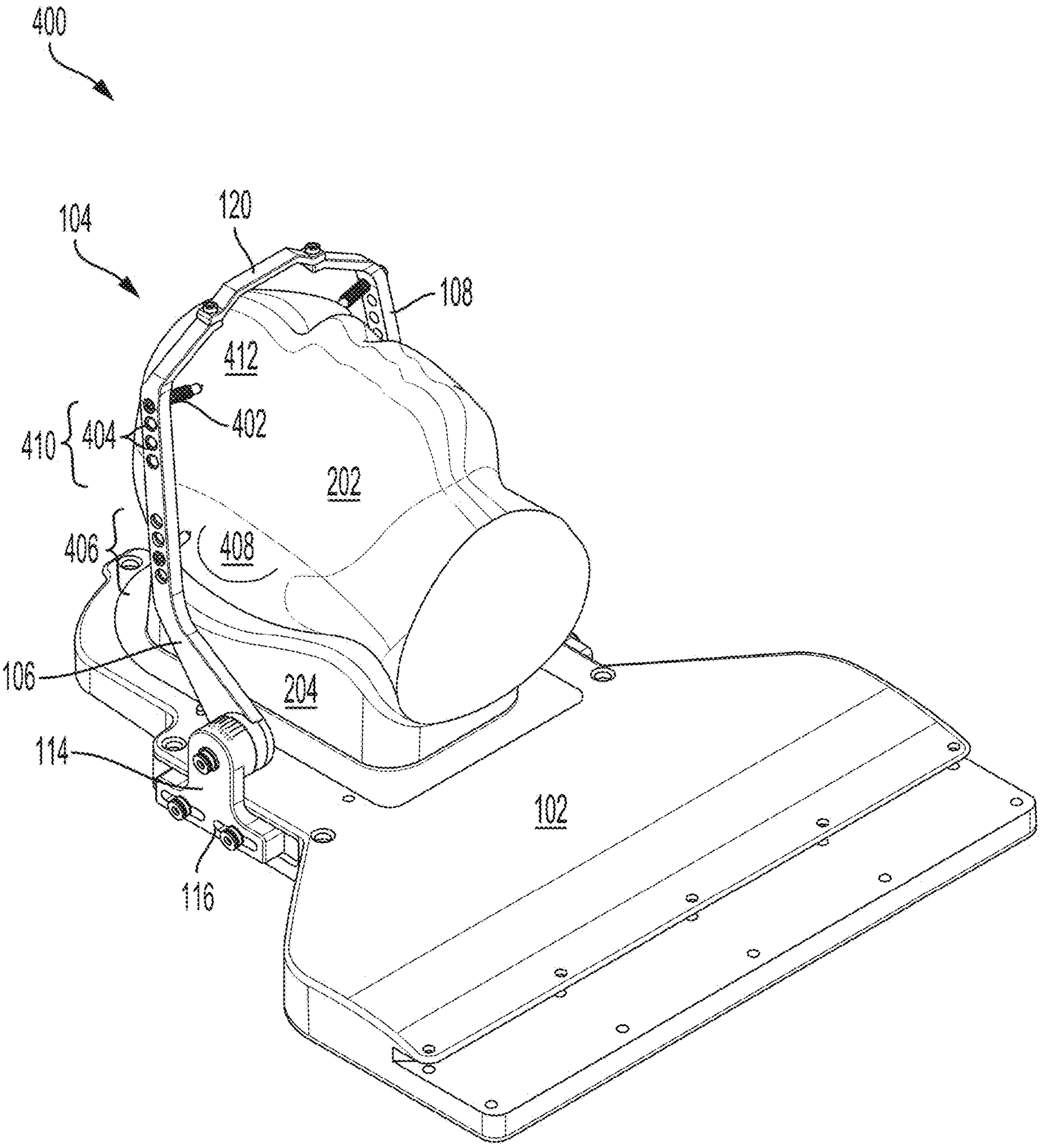
FIG. 4 is perspective drawing of an exemplary head immobilization device, in accordance with one aspect of the present disclosure.

FIG. 4 illustrates a patient head 202 is shown positioned in and engaged with a head immobilization device system 400. In various embodiments, the head immobilization device system 400 is used in combination with an image-based anatomy matching system using a predefined coordinate system. Fixation device 104 is adjustable relative to the base 102 to accommodate the patient's head 202 within the predefined coordinate system to immobilize the patient's head 202 within an externally defined coordinate system of the image-based anatomy matching system. As shown, the patient head 202 is positioned on a base 102 as described above. The fixation device 104, in particular the connecting portion 120 and the top portions of the right arm portion 106 and the left arm portion 108, extend across the patient head 202 when the patient is positioned on the base 102.

The head immobilization device system 200 may further include a head rest 204 disposed on the base 102. The head rest 204 may be configured to support the patient head 202 when the patient is positioned in the treatment system. In at least some embodiments, the head rest 204 is custom molded or otherwise custom fit to the patient's head to further facilitate immobilizing the patient's head when the patient's head is immobilized by the fixation device 104.

In various embodiments, one or more pins 402 the patient head 202 extend through apertures 404 on each of the right arm portion 106 and the left arm portion 108, as described above. Each aperture 404 is configured to receive a pin 402 therein for securing a position of the patient head 202 when the patient is immobilized by the head immobilization device system 400. For example, each pin 402 and each aperture 404 may include corresponding threaded portions such that the apertures 404 receive threads of the pins 402 for securing the pins 402 when positioned through the apertures 404.

Each pin 402 extends through an aperture 404 and engages the patient head 202 at an angle in a range between about 70 degrees and 110 degrees, inclusive, when the patient is immobilized by the head immobilization device system 400. In some embodiments, each pin extends through an aperture 404 and engages the patient head 202 at an angle of about 90 degrees. Each pin 402 has a major component in the horizontal direction with respect to a planar surface of the base 102. For example, each pin 402 extends out of an aperture 404 and engages the head where the pin 402 is mostly in a horizontal direction extending across the patient head 202 such that the head rest 204 is bearing the weight of the patient's head. The pin 402 configuration is in stark contrast to other head immobilization devices (such as stereotactic frames) which are angled substantially vertically to engage the patient's head when the patient is wearing the device such that the pins themselves bear the weight of the patient's head, thereby increasing trauma and discomfort to the patient's head. Additionally, because the fixation device 104 is adjustable to patient's head, the patient is not required to wear the head immobilization device described herein throughout a day of procedures (e.g., including the imaging and treatment procedures).

As shown, each of the right arm portion 106 and the left arm portion 108 include two sets of apertures 404. A more proximate set 406 (e.g., relative to the base 102) includes a number of apertures 404 so that an aperture can be selected for insertion of a pin to engage the bony protuberance above/behind an ear 408 on the patient's head 202. In various embodiments, a more proximate set 406 of apertures 404 is disposed on each of the right arm portion 106 and the left arm portion 108 of the patient head 202 so that a pin 402 inserted through one of the apertures engages the patient head 202 behind an ear 408 on each side of the patient head 202. A more distal set 410 (e.g., relative to the base 102) of apertures 404 is disposed at a temple 412 of the patient head 202. For example, a more distal set 410 of apertures 404 is disposed on each of the right arm portion 106 and the left arm portion 108 of the patient head 202 and a pin 402 engages each side of the temple 412 of the patient head 202. In various embodiments, sets of the apertures 404 are disposed on opposing sides of the temporalis muscle on each side of the patient's head 202.

Figure 5:
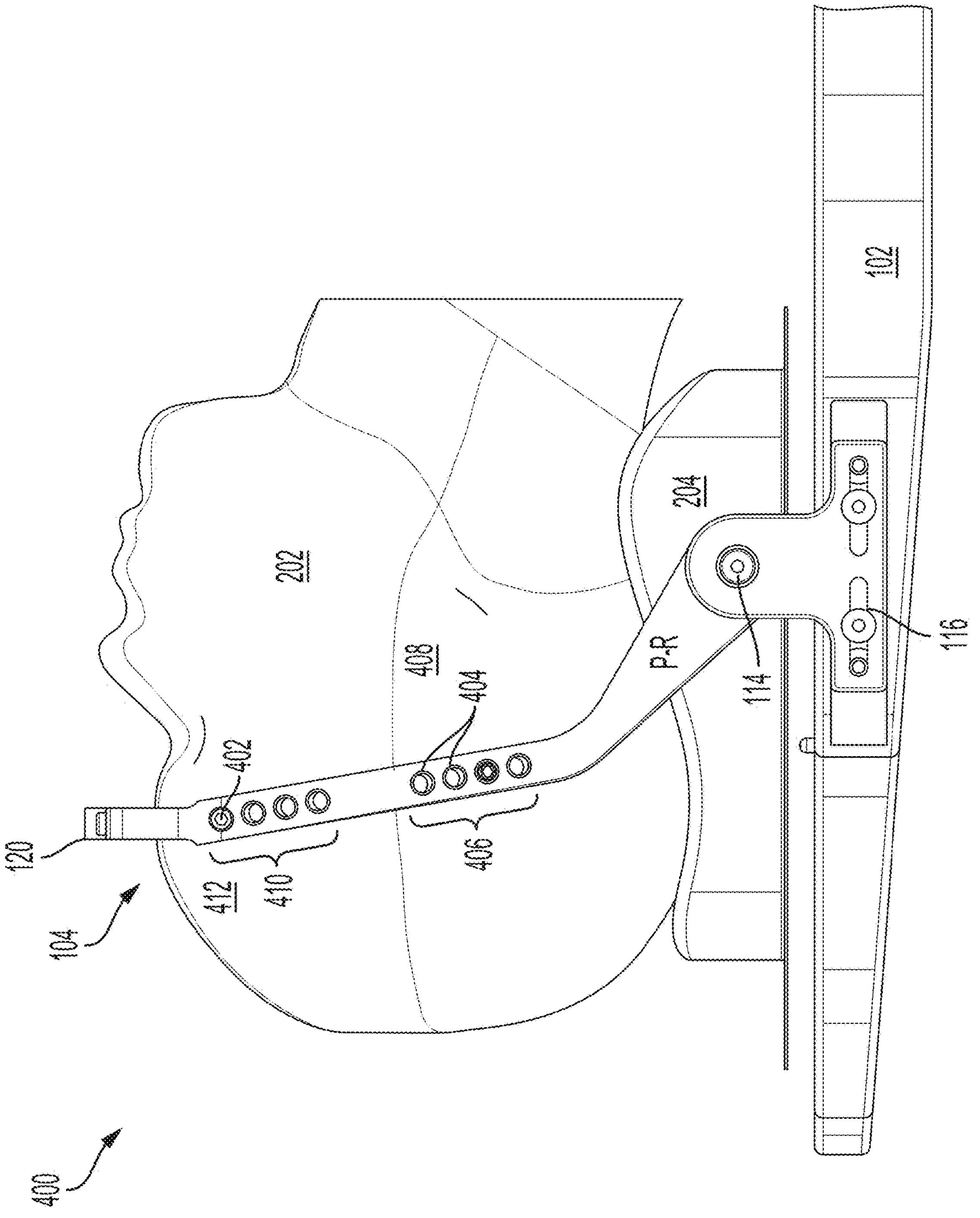
FIG. 5 is drawing of a side view of an exemplary head immobilization device, in accordance with one aspect of the present disclosure.
Figure 6:
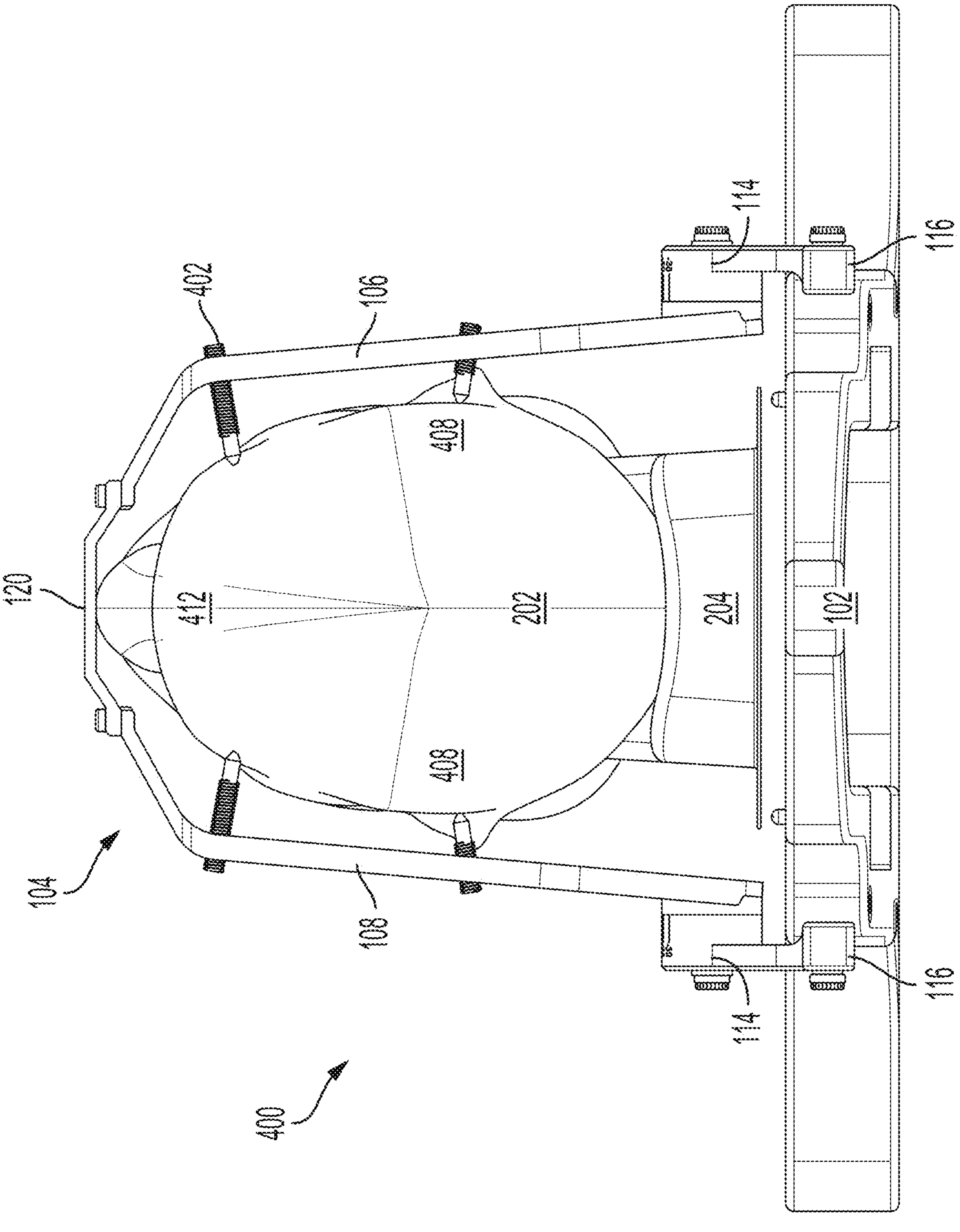
FIG. 6 is drawing of a posterior view of an exemplary head immobilization device, in accordance with one aspect of the present disclosure.

FIG. 5 illustrates a side view of the patient head 202 positioned in and engaged with the head immobilization device system 400. FIG. 6 illustrates a posterior view of the patient head 202 positioned in and engaged with the head immobilization device system 400. In this view, each rotational joint 114 and sliding joint 116 associated with the respective right arm portion 106 and left arm portion 108 are shown. Two pins 402 extend through the fixation device 104 (e.g., the respective right arm portion 106 and the left arm portion 108) to engage the patient head 202. As shown, pins 402 may be mirrored on each side of the patient head 202. In other embodiments, it is contemplated that alternative configurations of pins 402 on each side of a patient head 202 may be used. For example, more or less pins 402 may be used on the right arm portion 106 than the left arm portion 108, or vice versa. In another example, the pins 402 may be placed in different locations on the right arm portion 106 than the left arm portion 108, or vice versa, although the pins 402 are shown in mirrored locations on the right arm portion 106 and the left arm portion 108 in FIG. 6. In the embodiment shown, only one pin 402 is used for each set of apertures 314 such that two pins 402 on each side are sufficient to immobilize the patient's head 202. It is appreciated, however, that any number of pins 402 and configurations of pins 402 may be used. Advantageously, studies have shown that pins used with the head immobilization device system described herein may be less tight (e.g., apply less pressure to the patient's head) than other immobilization devices or fixations devices.

Figure 7:
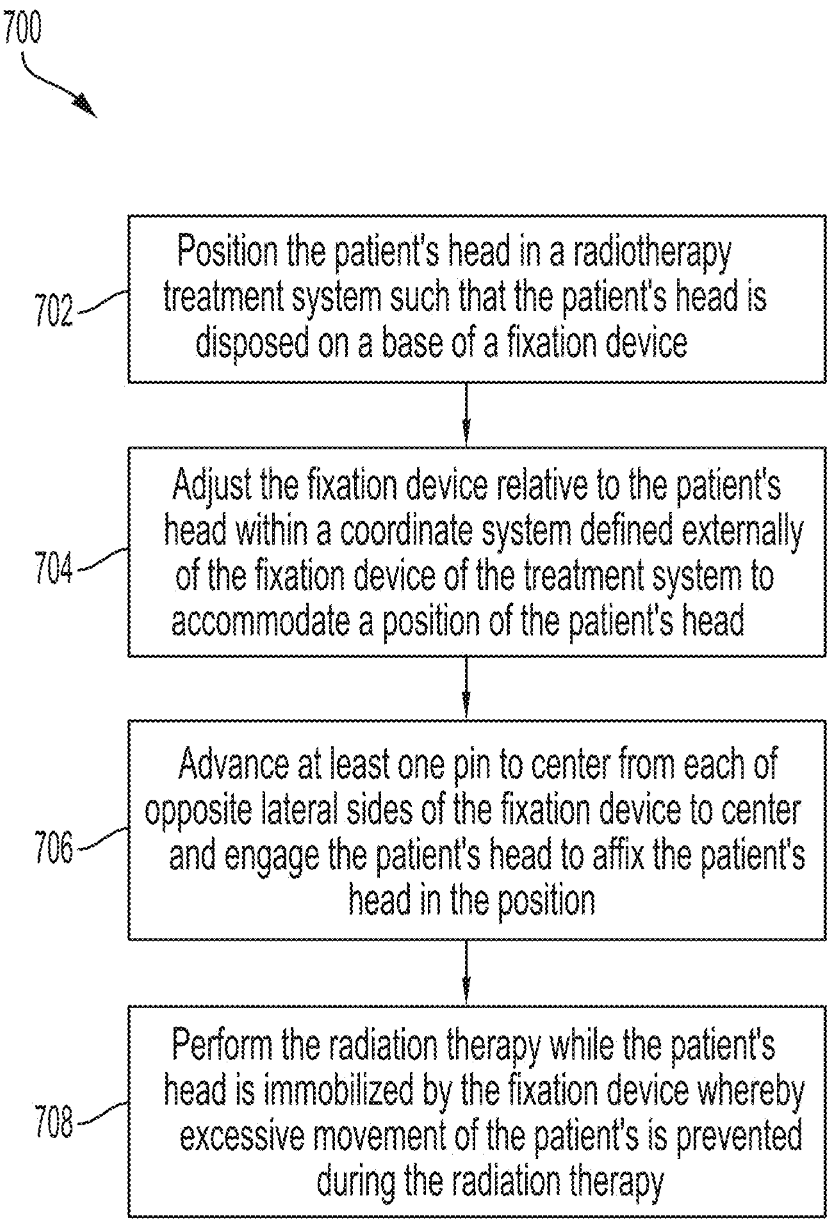
FIG. 7 is a flowchart of a method, in accordance with one aspect of the present disclosure.

FIG. 7 is a flowchart of a method 700 for immobilizing a head of a patient during a radiation therapy session. Method 700 includes operation 702. Operation 702 includes positioning the patient's head in a radiotherapy treatment system such that the patient's head is disposed on a base of an immobilization device. The immobilization device may be of the type described in detail herein including medical device 100, head immobilization device system 200, head immobilization device 300, head immobilization device system 400, etc. The patient's head may be positioned in a radio therapy treatment system such that the patient is not engaged with the immobilization device.

Operation 704 includes adjusting the fixation device relative to the patient's head within a coordinate system defined externally of the fixation device of the treatment system to accommodate a position of the patient's head. In particular, the fixation device does not define the frame of reference and is adjustable to any coordinate system, including a coordinate system defined externally of the fixation device (e.g., the coordinate system is defined by the treatment system). For example, adjusting a fixation device relative to the patient's head may include adjusting the fixation device within a predefined frame of reference of the treatment system to accommodate a position of the patient's head. In various embodiments, adjusting the fixation device includes adjusting an incline of the fixation device relative to the base where the base is substantially horizontal. For example, and as shown by base 102 described in FIG. 1, the base includes a substantially planar surface. The fixation device of the immobilization device is configured to be adjustable using a rotational joint at each side of the base where the fixation device meets the base. The rotational joint adjusts an incline of the fixation device such that the top portion of the fixation device (in some embodiments, the connection portion of the fixation device) moves forward or backward relative to the patient's head and/or the base. In some embodiments, the rotational joint may include markings indicative of the incline to facilitate the adjustment, as described above. In other embodiments, adjusting the fixation device further includes sliding the fixation device relative to the base. For example, in some embodiments, the fixation device is coupled to the base via a sliding joint which is configured to move the entire fixation device forward or backward relative to the patient's head and/or the base. The sliding joint may also include markings for indicating how far forward or backward the fixation device is slid.

Operation 706 includes advancing at least one pin to the center (e.g., of the fixation device) from each of opposite lateral sides of the fixation device and engaging the patient's head to immobilize the patient's head in the position. Advancing the pins to the center of the fixation device mechanically stabilizes the patient's head to facilitate immobilization of the patient's head. Importantly, the pins are not used to adjust the position of the patient's head. In various embodiments, pins known in the art may be advanced through apertures on each lateral side of the fixation device toward the center (e.g., toward the patient's head) to immobilize the patient's head. Various arrangements of one or more pins, as described above, may be used to immobilize the patient's head.

Operation 708 includes performing the radiation therapy while the patient's head is immobilized by the fixation device. In various embodiments, excessive movement of the patient's head is prevented or substantially reduced during the procedure when the patient's head is immobilized by the immobilization device described herein.

In various embodiments, method 700 further includes, prior to performing the radiation therapy, positioning the patient's head in a desired position, and adjusting a fixation device of another immobilization device within a predefined frame of reference of an imaging system. The desired position may be the same as the position described with respect to operation 702 described above. In at least some embodiments, another immobilization device may be used for an imaging procedure associated with the radiation therapy. For example, as would be understood by one having ordinary skill in the art, a patient may have to endure both an imaging procedure and the radiation therapy, often in the same day or substantially close in time. In at least some embodiments, to reduce cost and/or to increase comfort of the patient, another immobilization device may be used for the imaging process. The other immobilization device used for imaging may be a replica of the immobilization device used for radiotherapy and described with respect to operations 702 to 708. The replica is substantially the same in size and configuration as the immobilization device. The replica can be of the same general dimensions but made of a thinner material. In some embodiments, the replica is made out of plastic or other soft/flexible material which are relatively more cost effective than the material of the immobilization device used during radiotherapy. In some embodiments, the replica is a disposable or reusable. Method 700 may further includes performing an imaging process of the head of the patient using the replica immobilization device. In other embodiments, the same immobilization device may be used for both the imaging and the radiotherapy.

In at least some embodiments, method 700 may include disposing a mask between the patient and the fixation device during the imaging process and/or the radiation therapy. The mask may be an immobilization mask known in the art for reducing movement of a patient during imaging and/or radiation therapy. In one exemplary aspect, the mask is placed over the patient's head prior the imaging process and/or the radiation therapy and the fixation device is configured to be disposed on top of the mask. The mask can be modified to include holes for passage of the pins through the mask and against the patient's head.

Figure 8A:
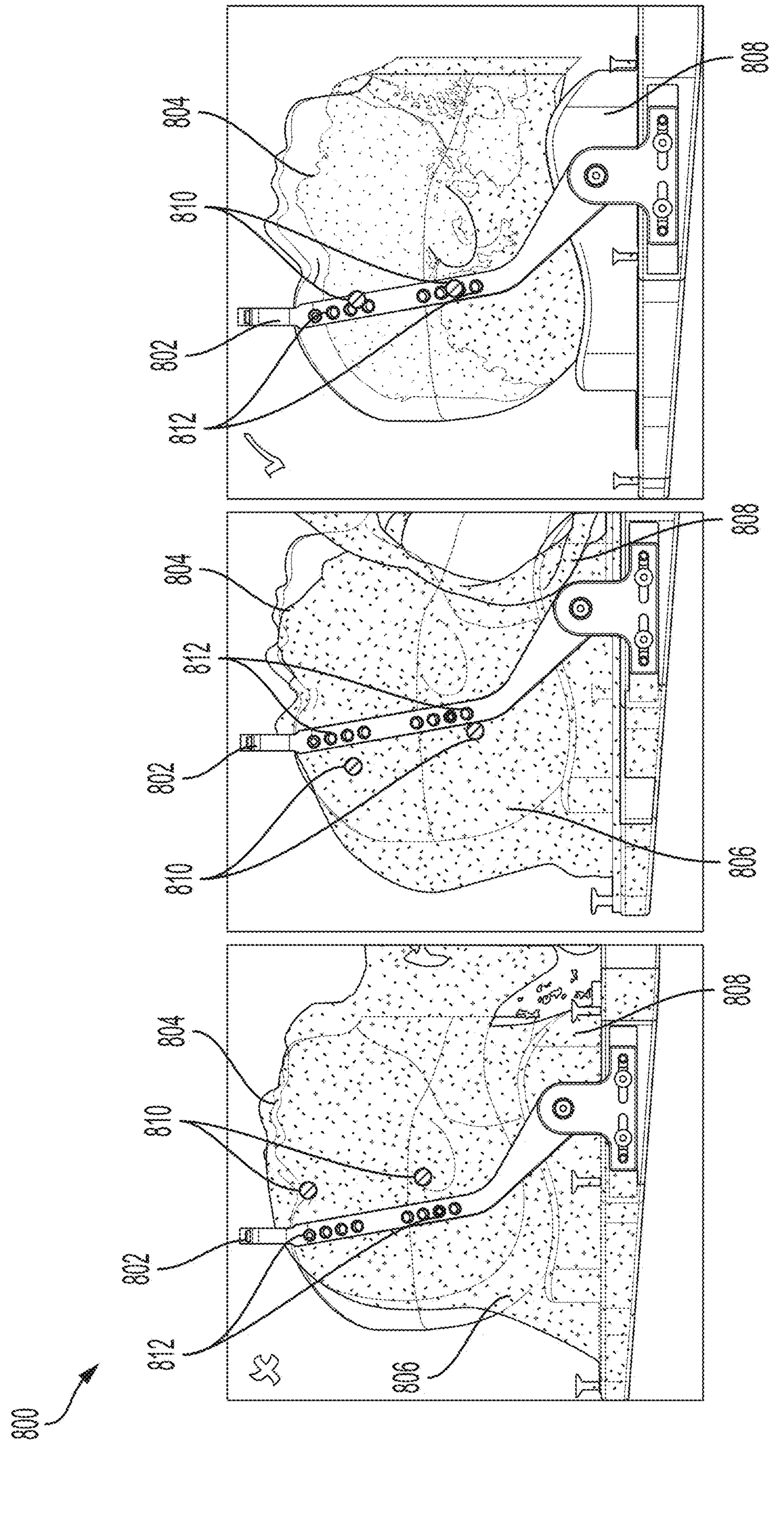
FIG. 8A illustrates exemplary setups, in accordance with one aspect of the present disclosure.

FIG. 8A illustrates examples of setups 800. As shown, a fixation device 802, such as any of the fixation devices described in detail above, is adjustable to immobilize the patient's head 804 during radiotherapy and/or imaging procedures. In this embodiment, a mask 806 is used to further used to facilitate immobilization, although it should be appreciated that in some embodiments, the fixation device 802 alone provides sufficient immobilization without the use of a mask 806. The patient's head 804 is further supported by a head rest 808. As illustrated in the left figure, the patient's head 804 is initially slightly inferior to the fixation device 802. For example, the target locations 810 on the patient's head 804 are slightly inferior to the apertures 812 disposed through the fixation device 802. In the middle figure of FIG. 8A, the patient's head 804 is slightly superior to the fixation device 802. For example, the target locations 810 on the patient's head 804 are slightly superior to the apertures 812 disposed through the fixation device 802, however, the fixation device 802 can be adjusted to accommodate this position of the patient's head. In the right figure, the patient is more optimally positioned in the pre-defined frame of reference of the radiotherapy system, which as shown, is slightly posterior but within an acceptable position to immobilize with the fixation device 802 as the arm portions can be positioned at the optimal locations on the patient's head for immobilization. In both instances shown in the second and third figures of FIG. 8A, fixation device 802 is adjustable to the patient's head 804 to immobilize the patient's head 804.

Figure 8B:
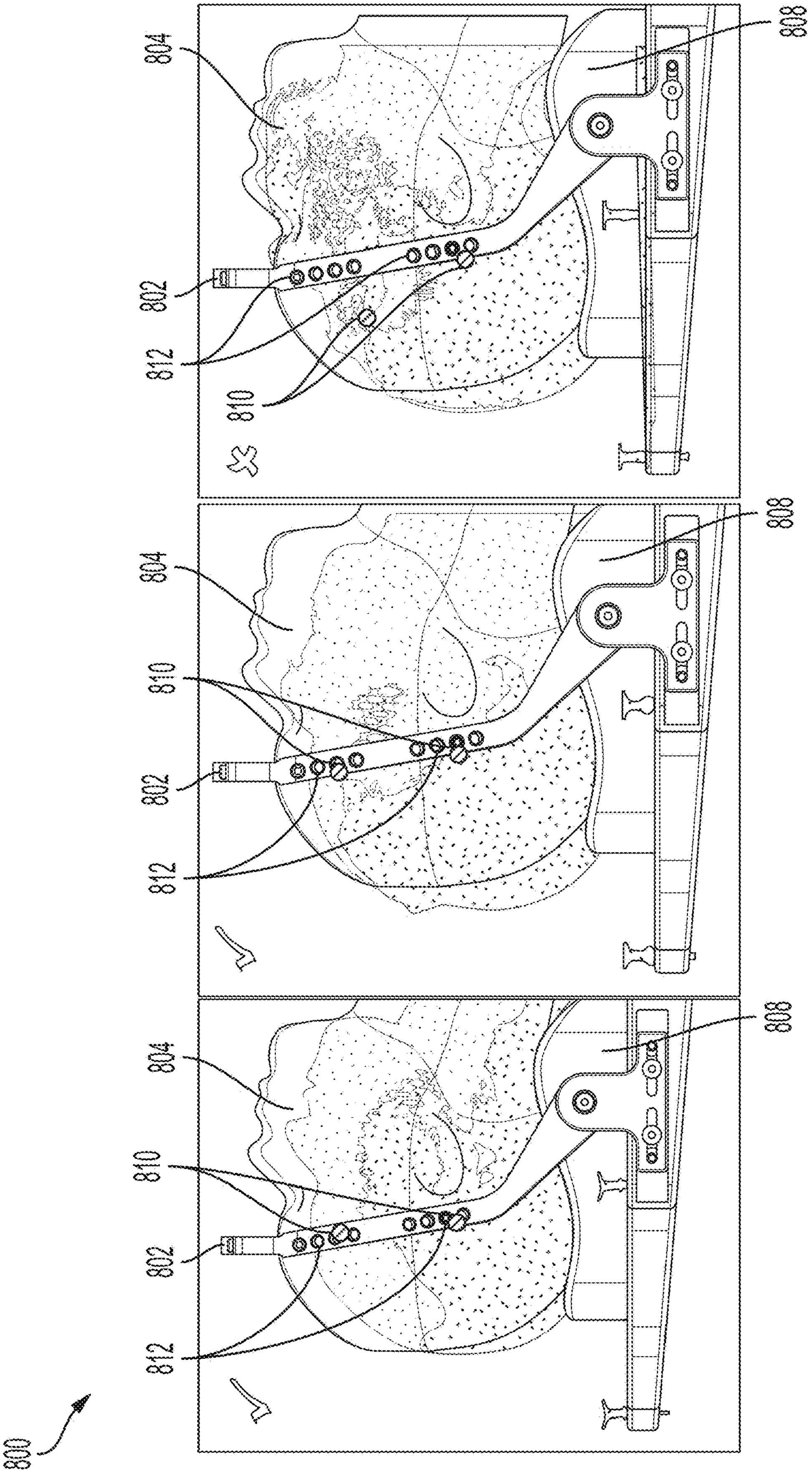
FIG. 8B illustrates exemplary setups, in accordance with one aspect of the present disclosure.

FIG. 8B illustrates examples of setups 800 without using a mask. For example, during an imaging procedure, such as CT imaging, a mask is an optional component. As shown, a fixation device 802, such as any of the fixation devices described in detail above, is adjustable to immobilize the patient's head 804 radiotherapy and/or imaging procedures. The patient's head 804 is further supported by a head rest 808. As illustrated in the first two figures of FIG. 8B, the fixation device 802 is positioned relative to the patient's head 804 to immobilize the patient's head 804 during radiotherapy or imaging. In the left figure, the patient's head is slightly posterior but the fixation device 802 can still adjust to the position of the patient's head for immobilization or to confirm the position/alignment of the fixation device during imaging to replicate during radiotherapy to immobilize the patient's head in the same position used during imaging. In the middle figure, the patient's head is more optimally positioned and again, the fixation device 802 can be adjusted to fit the patient's head at the designated locations. In the right figure, the patient's head is pitched up such that the target locations 810 on the patient's head 804 are posterior of the apertures 812 of the fixation device 802, such that repositioning of the patient's head to a more optimal position may be recommended. As shown, the fixation device 802 is adjustable to the patient's head 804 to immobilize the patient's head 804 during radiotherapy or to confirm proper alignment relative the device during imaging.

Figure 8C:
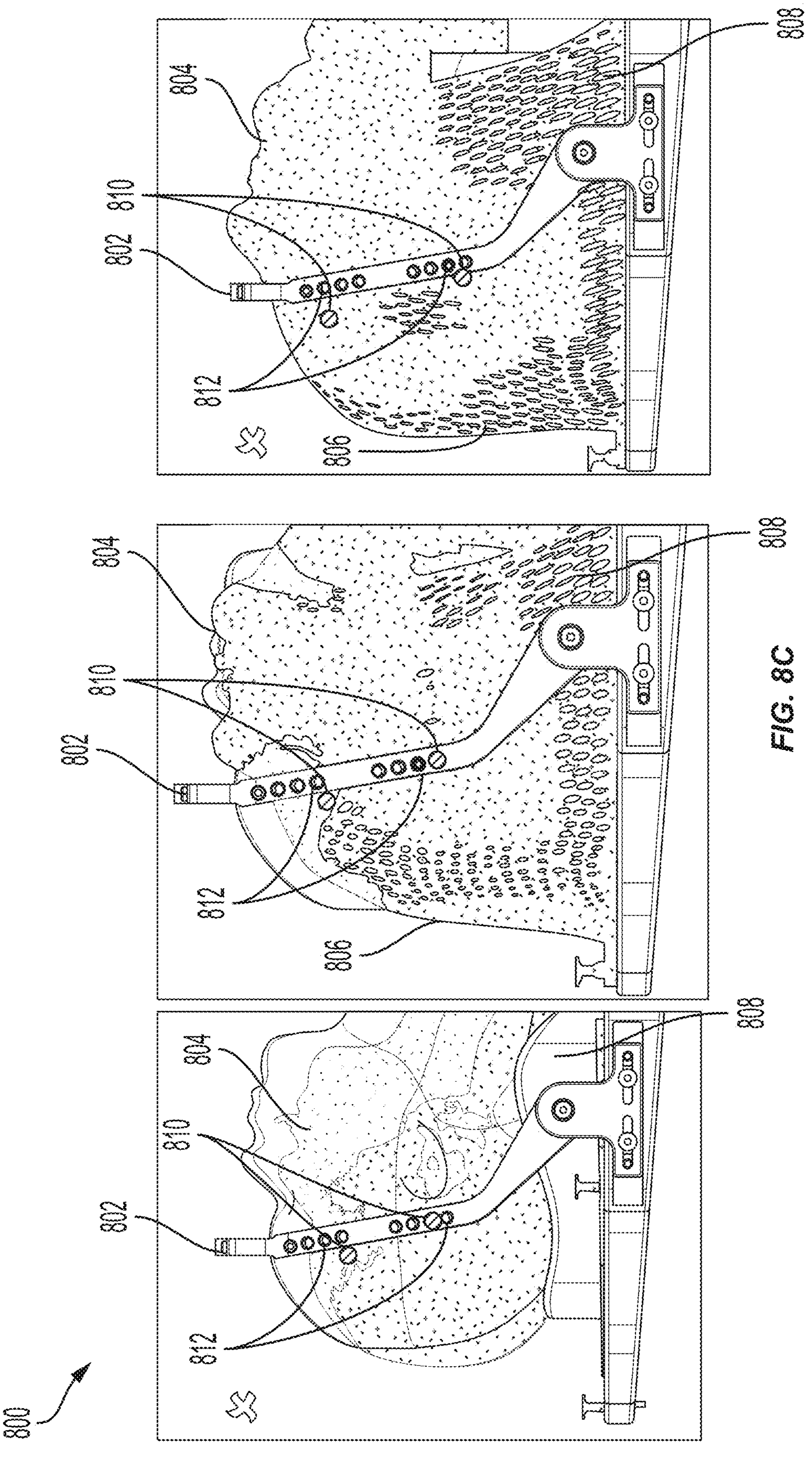
FIG. 8C illustrates exemplary setups, in accordance with one aspect of the present disclosure.

FIG. 8C illustrates additional examples of setups 800. As shown, a fixation device 802, such as any of the fixation devices described in detail above, is adjustable to immobilize the patient's head 804 radiotherapy and/or imaging procedures or to confirm positioning during imaging. In this embodiment, a mask 806 used to further used to facilitate immobilization, although it should be appreciated that the fixation device 802 alone provides sufficient immobilization without the use of a mask 806. The patient's head 804 is further supported by a head rest 808. As illustrated, in the first portion of FIG. 8C, the patient's head 804 is slightly posterior to the fixation device 802 as indicated by the position of the fixation device. For example, the target locations 810 on the patient's head 804 are slightly posterior to the apertures 812 disposed through the fixation device 802 such that repositioning of the patient's head may be recommended. Alternatively, a spacer, not shown, may be used to facilitate immobilization of the patient's head 804 by closing the gap between the patient's head 804 and the fixation device 802. The middle figure of FIG. 8C shows the patient's head 804 pitched up relative to the fixation device 802 but still in an acceptable position for the fixation device 802 to be adjusted to accommodate the patient's head for immobilization and/or confirmation of alignment of the device. In the third portion of FIG. 8C, a relatively larger patient is pitched up relative to the fixation device 802, which may be suggestive of the need to reposition the patient's head. As can be appreciated, the fixation device 802 is adjustable to the patient's head 804 in various positions to immobilize the patient's head 804 during radiotherapy and/or imaging, or to confirm alignment of the device at the patient's head position during imaging to replicate the same position during radiotherapy. It is appreciated that when the fixation device is used to confirm alignment/positioning during imaging that pins are not required, or dummy pins may be used that extend to the patient's head to confirm their positions at the designated points on the patient's head but are not driven to engage the patient's skull such as is done during immobilization.

Figure 9:
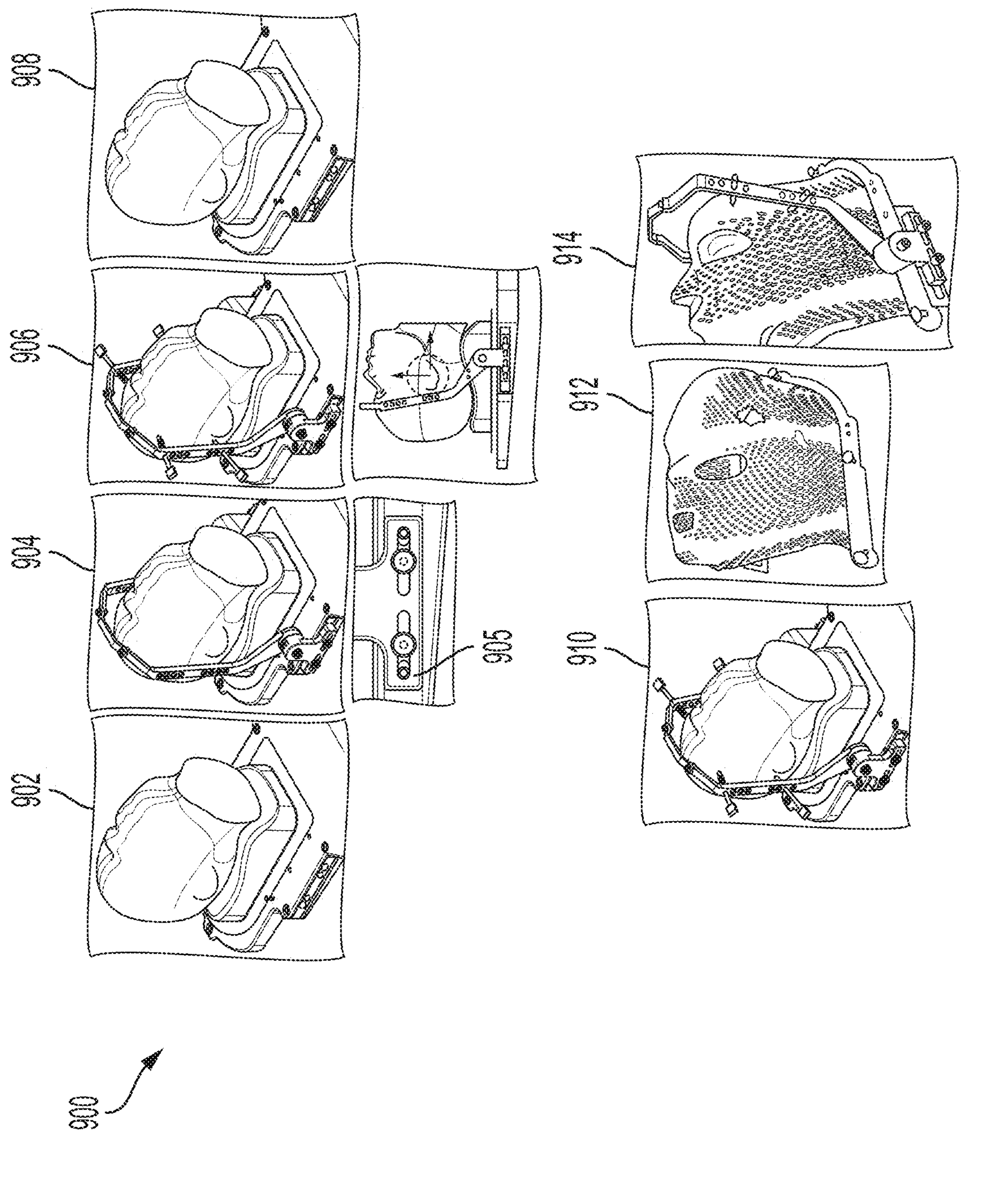
FIG. 9 illustrates an exemplary workflow, in accordance with one aspect of the present disclosure.

FIG. 9 illustrates an exemplary workflow 900 relating to imaging (e.g., CT imaging) using the immobilization device. Step 902 includes positioning a patient's head on a head rest, the head rest being positioned on a base of a fixation device, as described in detail above. For example, step 902 includes an initial set up of the patient. Step 904 includes installing the fixation device and adjusting the fixation device to the patient's head within a coordinate system defined by an imaging system to accommodate a position of the patient's head to facilitate immobilization of the patient's head during imaging, as described in various embodiments of the present disclosure. In some embodiments, the fixation device is initially set to a 0 degree angle (e.g., the left arm portion and right arm portion of the fixation device are substantially perpendicular to a planar surface of the base). In other words, the left arm portion and the right arm portion of the fixation device extend upwards at an angle of about 90 degrees relative to the planar surface of the base. In some embodiments, a sliding joint 905 is used to adjust the fixation device relative to the patient's head depending on whether the patient's head is initially superior or inferior to the fixation device (as shown and described with respect to FIGS. 8A-8C). Step 906 includes inserting pins to center and mechanically stabilize the patient's head within the fixation device. In some embodiments, the pin locations (e.g., pin sites) are marked by moving the patient and/or the fixation device in a superior and/or inferior direction (e.g., backward, or forward relative to the base). In various embodiments, dummy pins may be used to ensure the patient's head is properly centered. "Dummy pins" as used throughout the present disclosure may refer to pins only used for imaging and positioning the patient's head without engaging the patient's head. Following step 906, the patient's head may be imaged for a later radiotherapy treatment. Step 908 includes removing the fixation device and/or repositioning the patient's head on the base of the fixation device. In some embodiments, a mask 912 may be placed on the patient at step 908 and then reinstalling the fixation device as shown in Step 910 (mask not shown), checking the alignment, and inserting pins through apertures on the fixation device to center the patient's head within the fixation device and mark the locations on the mask that the fixation screws will pass through. Cut outs can be made in the mask at these locations so that, during a subsequent radiotherapy procedure, fixation screws of a same or similar immobilization device pass through the cut outs to immobilize the patient's head in the same position as the imaging, as shown in Step 914. In other embodiments, both the mask and the immobilization device can be used during imaging to immobilize the patient's head in a set position during imaging that can be readily replicated during radiotherapy by the mask and a same or similar immobilization device. In still other embodiments that do not require a mask, the immobilization device can be applied to center the patient's head in a set position during imaging, the position/alignment of the immobilization device is recorded so that the same position can be replicated during radiotherapy. In such embodiments, the immobilization device can utilize dummy pins that are not fully engaged to the patient's skull but aid in centering the patient's head and marking the locations for immobilization pins. In other embodiments, the immobilization device can utilize fixation pins that immobilize the patient's head during imaging.

Figure 10:
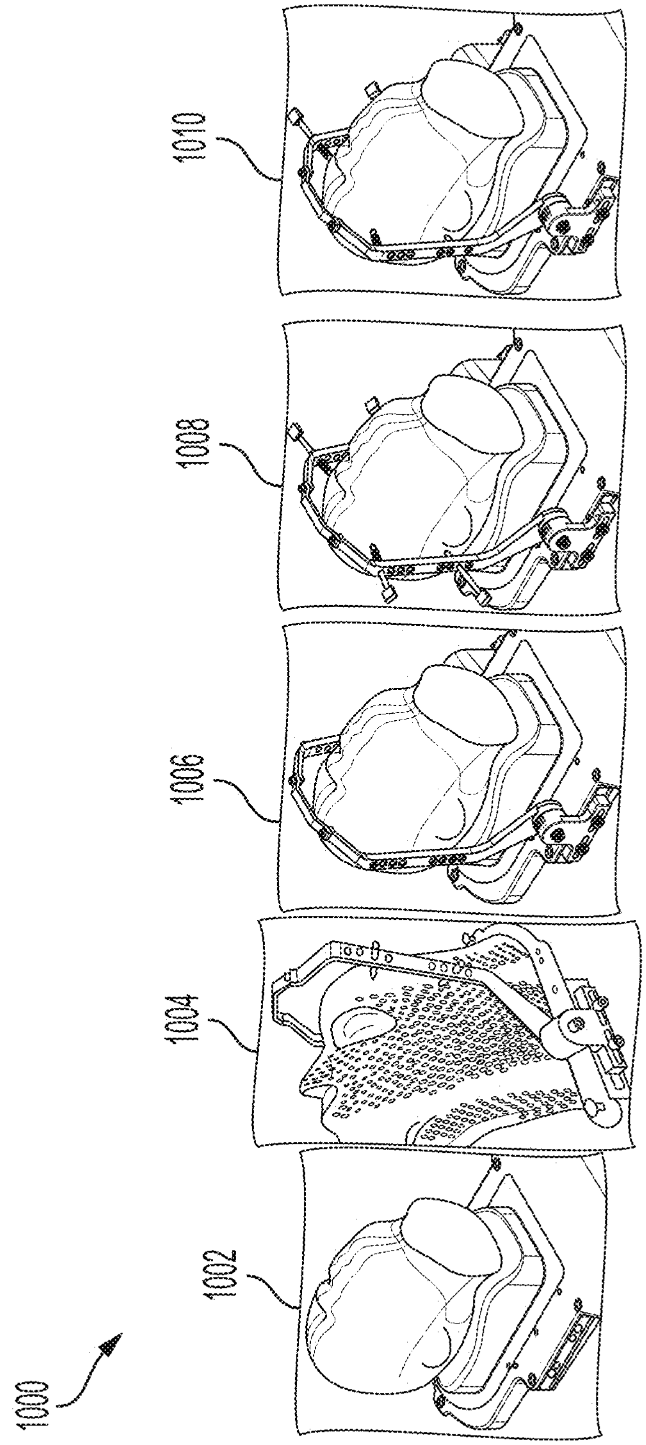
FIG. 10 illustrates an exemplary workflow, in accordance with one aspect of the present disclosure.

FIG. 10 illustrates an exemplary workflow 1000 relating to radiation treatment utilizing the immobilization device. Step 1002 includes positioning a patient's head on a head rest, the head rest being positioned on a base of a fixation device, as described in detail above. For example, step 1002 includes an initial set up of the patient. Step 1002 may include placing a deformable material (e.g., foam headrest, one or more layers of bubble wrap, etc.) under the patient. In various embodiments, workflow 1000 may include performing auto-align without the fixation device. Step 1002 may further include installing a mask on the patient, although, as previously noted, the use of the mask is optional as the fixation device can provide sufficient immobilization of the patient in some embodiments. Step 1004 includes installing the fixation device and adjusting the fixation device to the patient's head within a coordinate system defined by a radiotherapy system, the fixation device being adjustable to accommodate the set position of the patient's head to immobilize the patient's head during radiotherapy treatment, as described in various embodiments of the present disclosure. In some embodiments, one or more pins on each side of the mask may be removed to facilitate installation of the fixation device by sliding the immobilizer from the top. Step 1006 includes any final adjustments and torquing screws in the rotational and/or sliding joints on each side of the fixation device to lock the position of the fixation device relative to the patient's head (optional mask not shown). Step 1008 includes using a gauge pin to determine a correct pin length. For example, the gauge pin may be used to determine the length of the pins which extend through the fixation device and affix the patient's head. In some embodiments, the pins engage the head of the patient at an angle of about 90 degrees (or about 70 degrees to 110 degrees) from the surface of the head being engaged, thereby immobilizing the patient. Adjustment of the immobilization device (e.g., by rotation and sliding movement of the joints) allows the left and right arm portions to accommodate the set position of the patient's head within the coordinate system defined by the radiotherapy system. Step 1010 includes injecting local anesthesia at or near the pin-sites. In some embodiments, the pins may be finger tightened until the pins touch the skin of the patient's head and then the pins may be torqued to tighten. In some embodiments, the pins may be torqued to approximately 4 lb.-t-in. In various embodiments, the pins may be tightened simultaneously on both the left and right anterior sides and then on both the left and right posterior sides. This sequence may be repeated multiple times. Step 1010 includes inserting pins to center and mechanically stabilizing the patient's head within the fixation device. It is noted that in some embodiments, this workflow can be used with a treatment mask specially configured to allow passage of the pins therethrough. In other embodiments, this workflow can be used without any mask as the immobilization device itself provides sufficient immobilization of the patient. In some embodiments, the immobilization device used treatment can be the same or of substantially the same dimensions as the immobilization device used imaging so that a position during imaging can be replicated during treatment.

Figure 11:
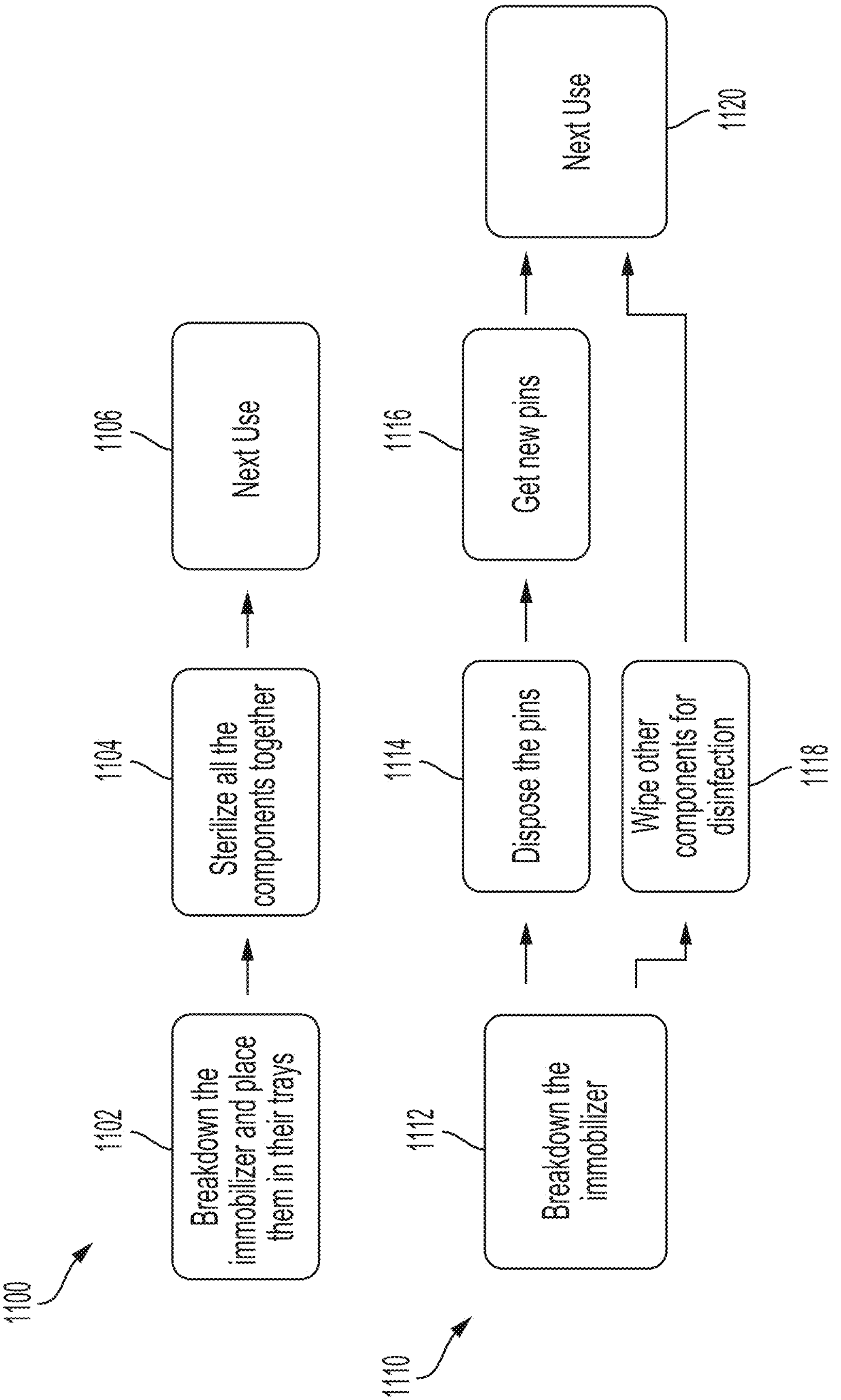
FIG. 11 illustrates an exemplary workflow, in accordance with one aspect of the present disclosure.

FIG. 11 illustrates an exemplary workflow 1100 and exemplary workflow 1110 for sanitizing components of the head immobilization system described herein. Exemplary workflow 1100 includes step 1102. Step 1102 includes breaking down the immobilizer (e.g., the fixation device) and placing the components in a sanitation tray. Step 1104 includes sterilizing all of the components together in the sanitation tray. Step 1106 includes reassembling the sanitized components of the fixation device and using the fixation device again.

Exemplary workflow 1110 similarly includes breaking down the immobilizer (e.g., the fixation device) and placing the components in a sanitation tray as step 1112. In some embodiments, step 1114 includes disposing the pins of the fixation device. Alternatively, in some embodiments, all components are sanitized in step 1118, as in step 1104 of workflow 1100. If the pins are disposed in step 1114, new pins may be retrieved in step 1116. The workflow 1110 proceeds to reassembling the sanitized components (with new pins or sanitized pins) and using the fixation device again in step 1120. Advantageously, the fixation device, as described throughout the present disclosure is relatively easy to sanitize and reuse relative to stereotactic frames which are cumbersome and difficult to disassemble for sanitation.

In the preceding specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It is recognized that the terms "comprising," "including," and "having," as used herein, are specifically intended to be read as open-ended terms of art. Further, the term "about" is interpreted to mean +/−10% of the respective value.

What is claimed is:

1. A head immobilization apparatus for immobilizing a patient's head in a radiotherapy treatment system during radiotherapy, the apparatus comprising:

a base configured for underlying a patient's head during radiotherapy;

a fixation device configured for immobilizing the patient's head during radiotherapy, wherein the fixation device is coupled to and extends upwards from the base, the fixation device comprising:

a left arm portion that extends alongside a left side of the patient's head and a right arm portion that extends alongside a right side of the patient's head when the fixation device is positioned on the patient's head for immobilization during radiotherapy;

one or more apertures disposed within each of the left arm portion and the right arm portion of the fixation device that are each aligned with the patient's head so that one or more pins extending through the one or more apertures engage the patient's head to facilitate immobilization during radiotherapy;

a first rotational joint through which the left arm portion is coupled to the base; and a second rotational joint through which the right arm portion is coupled to the base, wherein the rotational joints are configured to facilitate pivoting adjustment of the fixation device within a coordinate system defined by the radiotherapy treatment system to accommodate a position of the patient's head to facilitate immobilization of the patient's head during radiotherapy.

2. The apparatus of claim 1, wherein the left arm portion and the right arm portion form a unitary component.

3. The apparatus of claim 1, wherein the fixation device further comprises a connecting portion connecting the left arm portion and the right arm portion of the fixation device, the connecting portion being removably coupled to the left and/or right arm portions.

4. The apparatus of claim 1, further comprising a head rest disposed atop the base, wherein the head rest is configured to support the head of the patient when the patient is positioned on the base.

5. The apparatus of claim 2, further comprising a pivot mount connecting each arm portion to the base, wherein each pivot mount comprises the rotational joint.

6. The apparatus of claim 1, wherein the pivoting adjustment includes adjustment of an incline of the fixation device relative to the base.

7. The apparatus of claim 6, wherein one or both rotational joints of the left and right arm portions comprise markings indicative of the incline of the fixation device relative to the base.

8. The apparatus of claim 1, wherein the base comprises a planar surface.

9. The apparatus of claim 1, wherein the fixation device extends across the head of a patient when the patient is positioned on the base.

10. The apparatus of claim 1, wherein each of the left arm portion and the right arm portion of the fixation device comprises at least four apertures.

11. The apparatus of claim 1, wherein each of the left arm portion and the right arm portion of the fixation device comprises at least two sets of apertures.

12. The apparatus of claim 11, wherein a more proximate set is disposed behind an ear on the patient's head, wherein a more distal set is disposed at a temple on the patient's head.

13. The apparatus of claim 11, wherein each of the at least two sets of apertures comprise at least two apertures.

14. The apparatus of claim 11, wherein each of the at least two sets of apertures comprise at least four apertures.

15. The apparatus of claim 1, wherein each of the apertures are configured to receive a pin therein for securing a position of the head of the patient when the patient is immobilized by the apparatus.

16. The apparatus of claim 1, wherein the pins extend through the apertures and engage the head of the patient at an angle of greater than or equal to 90 degrees when the patient is immobilized by the apparatus.

17. The apparatus of claim 1, wherein each pin has a major component in a horizontal direction.

18. A method for immobilizing a head of a patient during a radiation therapy session comprising:

positioning the patient's head in a radiotherapy treatment system such that the patient's head is disposed on a base of a fixation device;

adjusting the fixation device relative to the patient's head within a coordinate system defined externally of the fixation device of the treatment system to accommodate a position of the patient's head;

advancing at least one pin from each of opposite lateral sides of the fixation device to center and engage the patient's head to affix the patient's head in the position; and performing the radiation therapy while the patient's head is immobilized by the fixation device whereby excessive movement of the patient's is prevented during the radiation therapy.

19. The method of claim 18, wherein adjusting the fixation device includes adjusting an incline of the fixation device relative to the base, the base being substantially horizontal.

20. The method of claim 18, wherein adjusting the fixation device further includes sliding the fixation device relative to the base.

21. The method of claim 18, further comprising, prior to performing the radiation therapy, positioning the patient's head in a desired position, adjusting a fixation device of another immobilization device within a predefined coordinate system of an imaging system; and performing an imaging process of the head of the patient.

22. The method of claim 21, wherein the other immobilization device used for imaging is a replica of the immobilization device used for radiotherapy, the replica being substantially the same in size and configuration as the immobilization device.

23. The method of claim 21, further comprising disposing a mask between the patient and the fixation device during the imaging process and/or the radiation therapy.

24. The method of claim 23, wherein the mask is placed over the patient's head prior to the imaging and/or the radiation therapy.

25. A treatment system, the system comprising:

an image-based anatomy matching system using a predefined coordinate system; and a head immobilization device, the head immobilization device comprising:

a base; and a fixation device, the fixation device being adjustable relative to the base to an external coordinate system to accommodate and immobilize a patient's head positioned within an externally defined coordinate system of the image-based anatomy matching system.

26. The system of claim 25, further comprising a head rest disposed on the base, wherein the head rest is configured to support the head of the patient when the patient is positioned in the treatment system.

27. The system of claim 25, wherein the fixation device further comprises a left arm portion that extends alongside a left side of the patient's head and a right arm portion that extends alongside a right side of the patient's head when the fixation device is positioned on the patient's head for immobilization during treatment.

28. The system of claim 27, wherein the fixation device further comprises a connecting portion connecting the left arm portion and the right arm portion of the fixation device, the connecting portion being removably coupled to the left and/or right arm portions.

29. The system of claim 27, wherein the fixation device further comprises a first a rotational joint through which the left arm portion is coupled to the base; and a second rotational joint through which the right arm portion is coupled to the base, wherein the rotational joints are configured to facilitate pivoting adjustment of the fixation device within a predefined frame of reference of the image-based anatomy matching system to accommodate a position of the patient's head to facilitate immobilization of the patient's head during treatment.

30. The system of claim 29, further comprising a pivot mount connecting each arm portion to the base, wherein each pivot mount comprises the rotational joint.

31. The system of claim 29, wherein one or both rotational joints of the left and right arm portions comprise markings indicative of an incline of the fixation device relative to the base.

32. The system of claim 27, wherein each of the left arm portion and the right arm portion of the fixation device comprises a plurality of apertures.

33. The system of claim 32, wherein each of the apertures are configured to receive a pin therein for securing a position of the head of the patient when the patient is immobilized by the fixation device.

34. The system of claim 33, wherein the pins extend through the apertures and engage the head of the patient at an angle greater than or equal to 90 degrees when the patient is immobilized by the fixation device.

35. The system of claim 25, wherein each pin extends in a direction having a major component in a horizontal direction.

* * * * *